United States Patent [19]

Kheiri

[11] Patent Number: 5,008,077
[45] Date of Patent: Apr. 16, 1991

[54] EASY HANDLING REAGENT STRIP

[75] Inventor: Mohammad A. Kheiri, Elkhart, Ind.

[73] Assignee: Miles Inc., Elkhart, Ind.

[21] Appl. No.: 457,106

[22] Filed: Dec. 26, 1989

[51] Int. Cl.⁵ .............................................. G01N 31/22
[52] U.S. Cl. ........................................ 422/56; 422/57;
422/58; 427/2; 435/805; 436/166; 436/169
[58] Field of Search ..................... 422/56, 58, 55, 61,
422/57; 435/805; 427/2; 436/166, 169

[56] References Cited
U.S. PATENT DOCUMENTS

| | | | |
|---|---|---|---|
| 3,901,657 | 8/1975 | Lightfoot | 422/56 |
| 3,979,184 | 9/1976 | Giaever | 422/57 |
| 4,160,008 | 7/1979 | Fenocketti et al. | 422/56 |
| 4,645,743 | 2/1987 | Baker et al. | 422/58 |
| 4,668,472 | 5/1987 | Sakamoto et al. | 422/58 |
| 4,687,529 | 8/1987 | Wang | 422/58 |
| 4,717,656 | 1/1988 | Swanljung | 422/58 |
| 4,826,759 | 5/1989 | Guire et al. | 422/58 |

Primary Examiner—Robert J. Warden
Assistant Examiner—Jill Johnston
Attorney, Agent, or Firm—Roger N. Coe

[57] ABSTRACT

An easily grasped reagent strip is disclosed. The reagent strip includes a handle that is elevated or spaced from a flat surface on which the reagent strip is placed. The handle is formed or bent to extend laterally from the rest of the reagent strip. Alternatively, ribs or buttons may be formed in the handle of the reagent strip to space the handle from a flat surface. The reagent strip can also include informative tactile indicia such as braille to inform a visually impaired or blind person of the type of reagent strip and the location of the reagent pad on the strip.

7 Claims, 3 Drawing Sheets

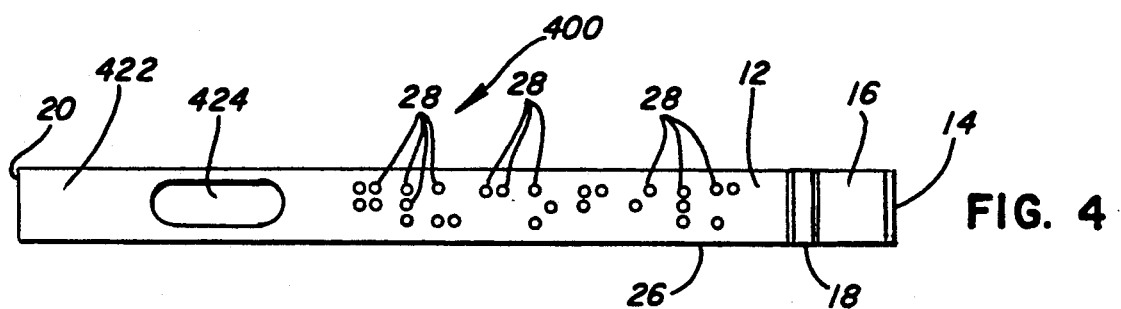
FIG. 4
FIG. 4A
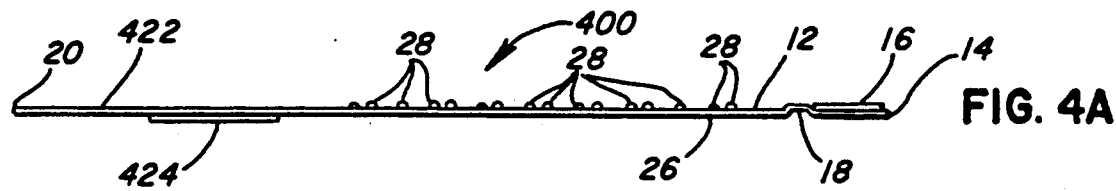
FIG. 5
FIG. 5A
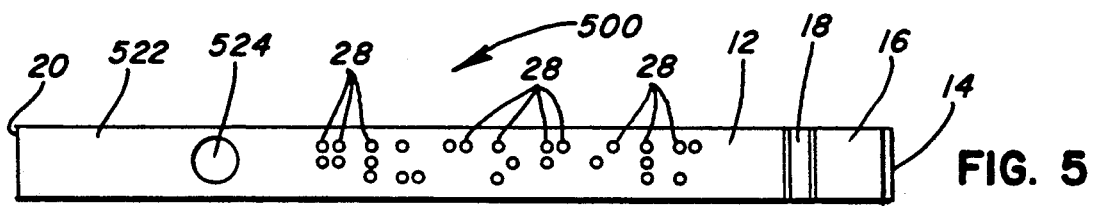
FIG. 6
FIG. 6A

EASY HANDLING REAGENT STRIP

BACKGROUND OF THE INVENTION

A. Field of the Invention

The present invention relates to a new and improved reagent strip; and more particularly, to a new and improved reagent strip that can be picked up easily from a flat surface such as a table and is capable of being packaged flat in the same manner as existing, difficult to pick up, reagent strips.

B. Description of the Background Art

Measuring a person's blood sugar or glucose level has become an every day necessity for many of the nation's seven million diabetics. Because this disorder can cause dangerous anomalies in blood chemistry and is believed to be a contributor to vision loss and kidney failure, most diabetics need to test themselves periodically and adjust their glucose count accordingly, usually with insulin injections. Patients who are insulin dependant-about 10 percent to 15 percent of diabetics-are instructed by doctors to check their blood sugar levels as often as four times daily.

For years the solution for diabetics was one of several urinanalysis kits that, despite repeated improvements, provided somewhat inaccurate measurements of glucose in the blood. Examples of early urine testing for glucose are described in U.S. Pat. Nos. 2,387,244 and 3,164,534. Later, reagent strips for urine testing were developed. Although reagent strips for urine testing are still in use today this testing procedure is limited in accuracy particularly since the renal threshold for glucose spillage into the urine is different for each individual. Moreover, sugar (glucose) in urine is a sign that the glucose was too high several hours prior to the test due to the time delay in glucose reaching the urine. Readings taken from urine, therefore, are indicative of the glucose level in the blood several hours before the urine is tested.

More accurate readings have been possible by taking readings using reagent strips and blood samples from patients to determine current glucose levels. Proper dosages of insulin are also more obtainable by increasing the frequency of taking readings of glucose levels in the blood. Consequently, the advent of home blood tests has been considered by some to be the most significant advance in the care of diabetics since the discovery of insulin in 1921.

Home blood glucose testing was made available with the development of reagent strips for whole blood testing. These reagent strips include a reactant system comprising an enzyme, such as glucose oxidase, capable of catalyzing the oxidation reaction of glucose to gluconic acid and hydrogen peroxide and a substance having peroxidative activity capable of catalyzing the oxidation of the indicator. The dye or indicator in the reagent pad of a reagent strip when exposed to blood turns a visually different shade of color and the shade is an indication of the glucose level in the blood sample.

In the past the reagent strips have been flat, straight rectangular pieces of plastic with a reagent pad secured to one end of the strip. Handling of these strips has been difficult for the aged or visually impaired and often times difficult even for the normal healthy individual in that a reagent strip when lying on a flat surface such as a table top is difficult to grasp. The flat reagent strips are also difficult to pick up if the strip is on a wet surface or when the user is in a hurry to wipe excess blood off the reagent pad or to read the glucose level in an instrument after a timed reaction. In addition, reagent strips are packaged in bottles and will often stick together making separation difficult by the user or patient.

SUMMARY OF THE INVENTION

Briefly, the present invention is directed to a new and improved reagent strip for use in testing blood samples; and specifically, for testing levels such as glucose in blood specimens. The reagent strip of the present invention is defined by a plastic carrier having a reagent pad at one end and a handle at the other end. The handle is thermally or cold pressure formed to provide a configuration wherein the handle extends laterally from the plane of the carrier. This can be accomplished by providing a gradual bend or curve to the handle, or by forming a transverse crease in the strip at a distance from one end. In the alternative, ribs or buttons may be thermoformed in the handle causing the handle to rock or be tilted on a flat surface allowing a user to pick up the handle easily. The reagent strip of the present invention can also include tactile indicia such as braille on the handle to allow visually impaired or blind persons to determine the type of strip and which side of the strip to apply a blood sample.

BRIEF DESCRIPTION OF THE DRAWINGS

The above and other advantages and novel features of the present invention will become apparent from the following detailed description of preferred embodiments of the invention illustrated in the accompanying drawings wherein:

FIG. 4 is a top plan view of a third alternative embodiment of a reagent strip constructed in accordance with the principles of the present invention;

FIG. 4A is a side elevation view of the reagent strip illustrated in FIG. 4;

FIG. 5 is a top plan view of a fourth alternative embodiment of a reagent strip constructed in accordance with the principles of the present invention;

FIG. 5A is a side elevation view of the reagent strip illustrated in FIG. 5;

FIG. 6 is a top elevation view of a fifth alternative embodiment of a reagent strip constructed in accordance with the principles of the present invention;

FIG. 6A is a side elevation view of the reagent strip illustrated in FIG. 6;

Figure 1:
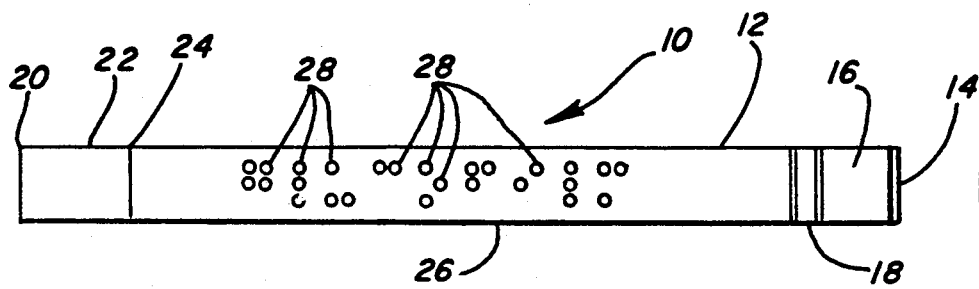
FIG. 1 is a top plan view of a reagent strip constructed in accordance with the principles of the present invention.

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DESCRIPTION OF THE PREFERRED EMBODIMENTS

Figure 1A:
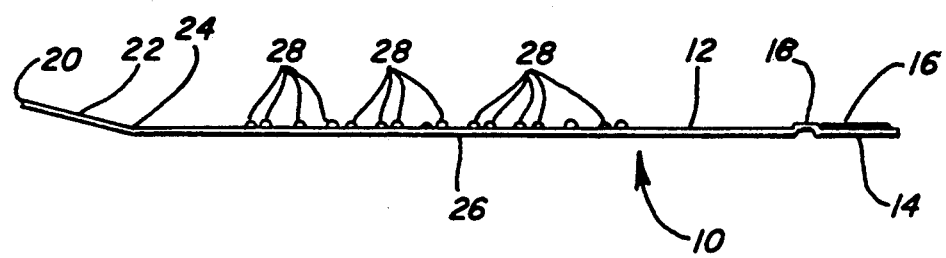
FIG. 1A is side elevation view of the reagent strip illustrated in FIG. 1.

Referring initially to FIGS. 1 and 1A, there is illustrated a reagent strip generally designated by the reference numeral 10 constructed in accordance with the principles of the present invention. It is to be noted that the present invention has applicability to all reagent strips and test devices and the reference herein to blood glucose test strips is merely for illustrative purposes. The reagent strip 10 includes a carrier 12 fabricated of a plastic material such as Trycite TM or a similar flexible, inexpensive material. The carrier 12 includes a first end 14 to which is secured a reagent pad 16. The reagent pad 16 is a typical reagent pad including a reactant system with an enzyme, such as glucose oxidase, capable of catalyzing the oxidation reaction of glucose to gluconic acid and hydrogen peroxide, an indicator or oxidizable dye and a substance having a peroxidative activity capable of catalyzing the oxidation of the indicator. A ridge or barrier 18 is formed in the carrier 12 to separate or to form a barrier between the reagent pad 16 and the remaining portion of the reagent strip 10. The ridge or barrier 18 is an optional feature and is not required for the design, function or operation of the strip 10.

The carrier 12 also includes a second end 20 defining an easily grasped handle 22. A bend or crease 24 is thermally or cold pressure formed in the carrier 12 to define the handle 22. The bend or crease 24 is at a selected distance inwardly of the second end 20 along the carrier 12. The formation of the bend or crease 24 results in the handle 22 being displaced laterally of the plane of the carrier 12.

As will be understood, if the reagent strip 12 is placed on a flat surface such as a table, the handle 22 is easily grasped by a user and the reagent strip 10 lifted from the table. If the reagent strip 10 is laid upside down on a flat surface the handle 22 will maintain a portion of the reagent strip 10 above the flat surface allowing the reagent strip 10 to be grasped easily. In this way, the reagent strip 10 is easily grasped by an older or invalid person or a person in a hurry.

Due to the resiliency of the plastic material from which the carrier 12 is made, the reagent strip 10 may be packaged in a foil package in the same manner as existing reagent strips which are flat along their full length. While the reagent strip 10 is packaged in a foil package, the handle 22 will be straightened out and flat in the package. The reagent strip 10 can also be packaged in a bottle. As the package is opened by a user, the natural resiliency of the plastic material of carrier 12 will cause the handle 22 to return to its normal orientation as illustrated in FIG. 1A. Thus, although the reagent strip 10 is packaged normally, it retains its resiliency and immediately returns to its easy grasping configuration upon opening of the package.

A generally flat body portion 26 of the reagent strip 10 is defined between the bend 24 and the barrier 18. Tactile indicia in the form of a plurality of bumps or holes 28 can, if desired, be formed in the body portion 26 to assist visually impaired and blind persons to determine the type of the reagent strip and which side of the strip the blood sample is to be applied. Although the tactile indicia 28 is illustrated as being formed on the body 26, it may be formed on either side of the carrier 12 or in the handle 22.

The handle 22 and the tactile indicia 28 also assist in preventing the reagent strips 10 from sticking together when packaged or stacked. This prevention of sticking also enhances the packaging of reagent strips 10 in bottles. Due to the handle 22 and the tactile indicia 28, the reagent strips 10 can be stacked parallel in a cartridge or cassette useable in an automatic or semiautomatic reading instrument.

Figure 2:
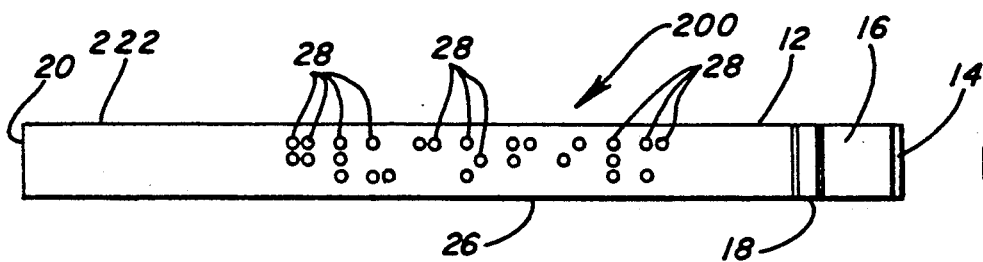
FIG. 2 is a top plan view of a second embodiment of a reagent strip constructed in accordance with the principles of the present invention.
Figure 2A:
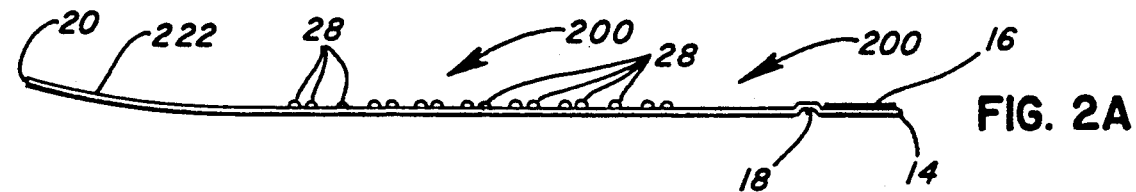
FIG. 2A is a side elevation view of the reagent strip illustrated in FIG. 2.
Figure 3:
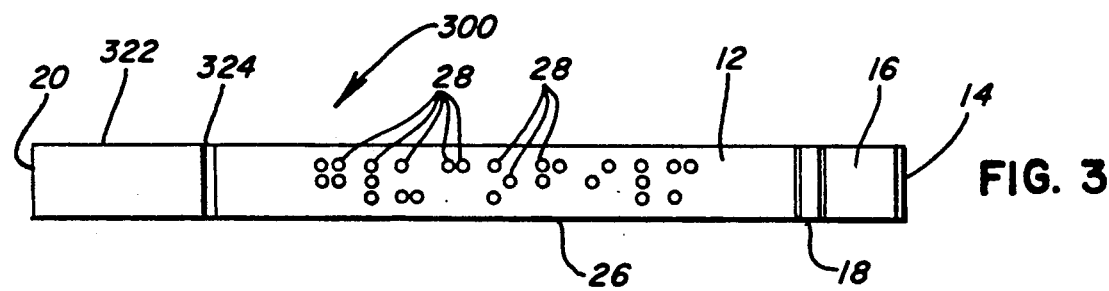
FIG. 3 is a top plan view of a second alternative embodiment of a reagent strip constructed in accordance with the principles of the present invention.
Figure 3A:
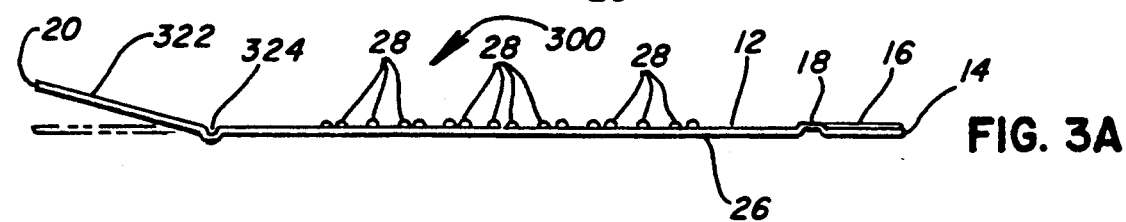
FIG. 3A is a side elevation view of the reagent strip illustrated in FIG. 3.

Two alternative embodiments of the reagent strip 10 are illustrated in FIGS. 2-3A. In these alternative embodiments the components that are identical to components in reagent strip 10 are indicated by the same reference numerals set forth in FIGS. 1 and 1A. Referring initially to FIGS. 2 and 2A, there is illustrated a first alternative reagent strip 200. The reagent strip 200 differs from reagent strip 10 in that instead of a crease or bend 24 in the carrier 12, the handle 222 of reagent strip 200 is formed with a curvilinear or bowed configuration. The handle 222 extends laterally from the plane defined by the body 26 of the carrier 12. The same desired result of easy grasping of the handle 222 is provided in the reagent strip 200 due to the curvilinear configuration.

Referring now to FIGS. 3 and 3A, a second alternative reagent strip 300 is illustrated. The reagent strip 300 is similar to the reagent strip 10 in that a thermally or cold pressure formed hinge or crease 324 is formed in the carrier 12 displacing a handle 322 laterally from the plane of the body 26. The handle 322 functions similarly to the handles 222 and 22 to allow the reagent strip 300 to be easily grasped by a user.

Turning now to FIGS. 4-6A and initially to FIGS. 4 and 4A, there is illustrated a different version of the reagent strip 10 in that a spacer or raised portion is provided to allow the handles of these reagent strips to be easily grasped. With specific reference to FIGS. 4 and 4A, there is illustrated a reagent strip 400. This reagent strip 400 includes several components that are identical to the components identified in FIGS. 1-3A and these components are identified by the same reference numerals appearing in FIGS. 1-3A. The reagent strip 400 differs from the reagent strips 10, 200 and 300 in that the handle 422 does not extend laterally from the plane of the body 26. In place of the displacement of the handle, the handle 422 includes a thermally or cold pressure formed ridge 424. The ridge 424 is elongated along the longitudinal axis of the carrier 12. The ridge 424 is longer than it is wide and extends outwardly from the side of the carrier 12 opposite the side of the carrier 12 on which the reagent pad 16 is secured. If the reagent strip 400 is placed on a flat surface such as a table with the ridge 424 against the surface, the elongated ridge 424 maintains the handle 422 and specifically the end 20 above the flat surface or table a distance equal to the thickness of the ridge 424. This allows the end 20 to be grasped by a user and lifted from the table or flat surface. In addition, due to the elongated configuration of the ridge 424, the reagent strip 400 can be rocked side to side about the longitudinal axis of the ridge 424 allowing even easier gripping or access to the end 20 of the reagent strip 400.

A variation of the reagent strip 400 is illustrated in FIGS. 5 and 5A. This reagent strip 500 includes a thermally or cold pressure formed circular button 524 in a handle 522. The button 524 functions in the same manner as the ridge 424 in that it maintains the handle 522 elevated relative to a flat surface such as a table. In addition, the circular configuration of the button 524 allows the handle 522 to be rocked on a flat surface such as a table top to allow even easier gripping of the handle 522.

A further version of a reagent strip of the present invention is provided in the reagent strip 600 illustrated in FIGS. 6 and 6A. The reagent strip 600 includes a thermally or cold pressure formed ridge 624 similar to the ridge 424 except that the ridge 624 is oriented diagonally on the handle 622 of the reagent strip 600. Similar to the ridge 424, the diagonal ridge 624 maintains the handle 622 above a flat surface such as a table and allows rocking of the handle 622 for easier grasping of the handle 622.

Figure 7A:
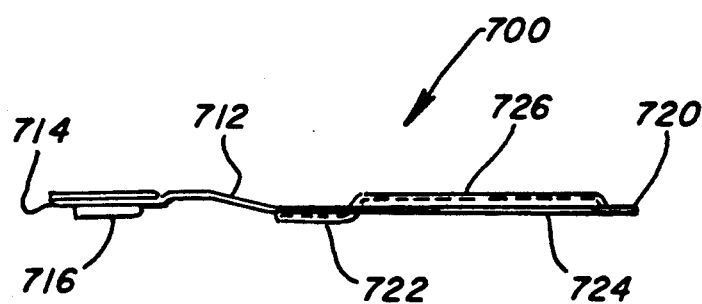
FIG. 7A is a side elevation view of the reagent strip illustrated in FIG. 7.
Figure 7:
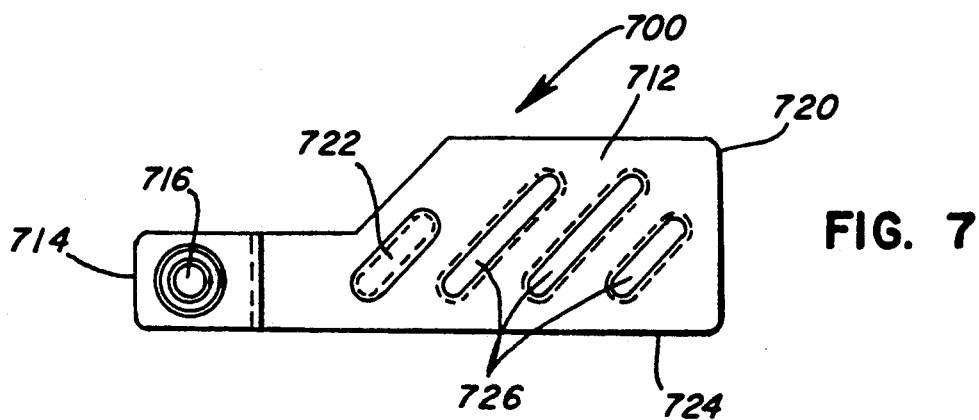
FIG. 7 is a top plan view of a sixth alternative embodiment of a reagent strip constructed in accordance with the principles of the present invention.

A still further embodiment of a reagent strip constructed in accordance with the principles of the present invention is the reagent strip 700 illustrated in FIGS. 7 and 7A. The reagent strip 700 includes a plastic carrier 712 that is shaped in a key-shaped configuration. The plastic carrier 712 includes a first end 714. A reagent pad 716 is secured to the first end 714. A thumb stop 722 is formed in and extends above the carrier 712. In addition, several ribs 726 are formed in a handle 724 of the reagent strip 700. These ribs 726 are recessed and extend downwardly from the carrier 712. The ribs 726 function to maintain the handle 724 spaced above a flat surface such as a table when the reagent strip 700 is placed on the flat surface. The ribs 726 allow the reagent strip 700 to be easily grasped by a patient or user.

Each of the reagent strips 10, 200, 300, 400, 500, 600, and 700 discussed above can be easily grasped by an older or physically impaired person as well as a person who is in a hurry to take measurements or comply with the timing requirements for testing glucose in blood. This easy grasping feature can be inexpensively incorporated into a reagent strip, and the reagent strips can be packaged in the same manner as prior art strips.

I claim:

1. A reagent strip, comprising:
    an elongated carrier,
    a diffusion reagent area on a first portion of said elongated carrier, and
    an elongated handle constituting a second portion of said elongated carrier;
    wherein said elongated handle includes at least one projection extending downwardly from said plane to render said reagent strip susceptible to tipping on a flat surface.

2. The reagent strip set forth in claim 1 wherein said projection constitutes one or more button like projection.

3. The reagent strip set forth in claim 1 wherein said projection constitutes one or more rib like projection.

4. A unitary reagent strip, comprising:
    a carrier having an elongated planar body with an upper and a lower surface, a first end and a second end; and
    a reagent area on the upper surface of said first end of said carrier;
    wherein said second end is permanently positioned to extend upwardly at an angle from the plane defined by said elongated planar body of said carrier.

5. A method of forming a reagent strip, comprising the steps of:
    forming an elongated planar carrier defining a body of a reagent strip, said elongated planar carrier having a first end portion and a second end portion;
    securing a dry reagent pad to said first end portion of said elongated planar carrier; and
    forming at least one projection on said second end portion to extend downwardly from the plane of said elongated planar carrier to render the reagent strip susceptible to tipping on a flat surface.

6. A method of forming a solid state reagent strip that can be lifted easily from a planar surface, comprising the steps of:
    forming an elongated carrier, said elongated carrier including a first end and a second end;
    securing reagent to said first end of said elongated carrier; and
    forming a crease in said second end of said elongated carrier, wherein said second end of said elongate carrier extends at the crease upwardly from the plane of said elongated carrier to render the reagent strip susceptible to tipping on a planar surface.

7. A method of producing a reagent strip that is easily grasped and lifted from a flat surface, the steps comprising:
    forming (a) a substantially flat carrier defining a first end portion, (b) an elongated second end portion and (c) a body portion between said first end portion and said elongated second end portion;
    securing a dry reagent pad to said first end portion, and
    forming a raised element on said elongated second end portion, which raised element extends downwardly from the plane of the substantially flat carrier.

* * * * *